United States Patent [19]
Considine

[11] 3,981,621
[45] Sept. 21, 1976

[54] BEARING WEAR DETECTION DEVICES
[75] Inventor: William Howard Considine, Storrington, England
[73] Assignee: The A.P.V. Company Limited, Crawley, England
[22] Filed: Mar. 27, 1975
[21] Appl. No.: 562,868

[52] U.S. Cl. ............................. 417/44; 116/124 A; 116/DIG. 21; 308/1 A; 415/10; 415/118; 417/423 R
[51] Int. Cl.² ........................................ F04B 49/06
[58] Field of Search ................ 417/1, 12, 13, 24, 9, 417/44, 423 R; 308/1 A, 72, 63, 10; 116/115, 124 A, DIG. 21; 415/10, 118

[56] References Cited
UNITED STATES PATENTS

| | | | |
|---|---|---|---|
| 2,941,120 | 6/1960 | Harman et al. | 417/42 X |
| 2,960,938 | 11/1960 | Williams | 417/13 |
| 2,985,010 | 5/1961 | Piltz | 417/1 |
| 3,486,479 | 12/1969 | Hartmann | 116/115 |
| 3,565,495 | 2/1971 | Lyman | 308/10 |

FOREIGN PATENTS OR APPLICATIONS

| | | | |
|---|---|---|---|
| 516,658 | 9/1955 | Canada | 308/1 A |
| 622,055 | 6/1961 | Canada | 308/1 A |

*Primary Examiner*—William L. Freeh
*Assistant Examiner*—Edward Look
*Attorney, Agent, or Firm*—Christel & Bean

[57] ABSTRACT

A sealed pump having a rotor and a stator and including an electromagnetic system comprising magnet means and a coil mounted on the rotor and stator and arranged such that a voltage is induced in the coil when the rotor rotates eccentrically, with the said voltage depending on the eccentricity.

14 Claims, 12 Drawing Figures

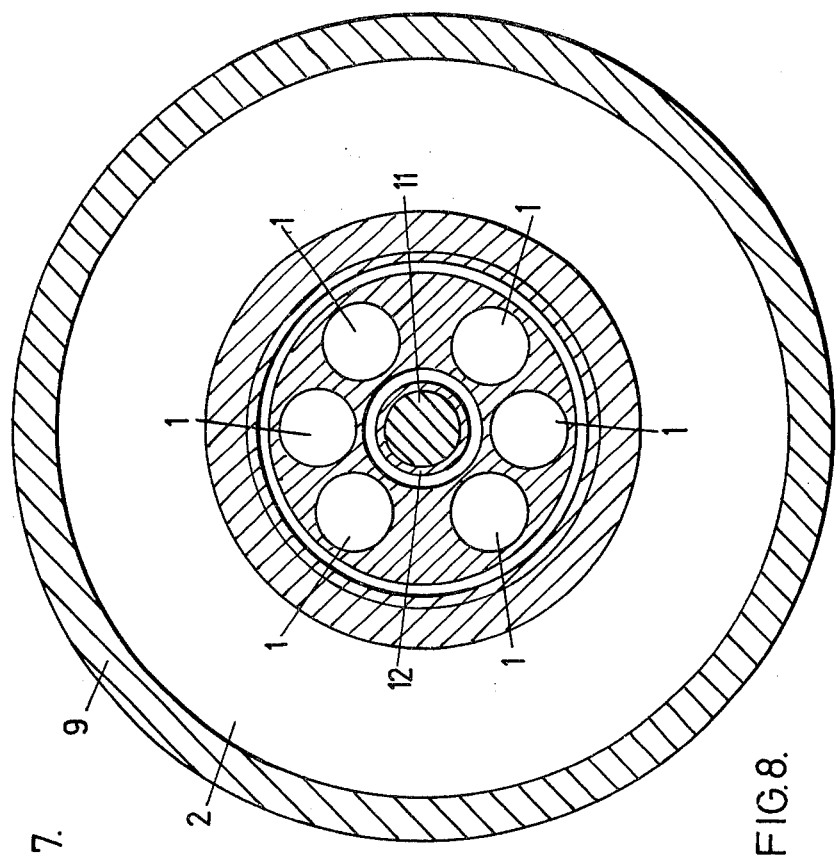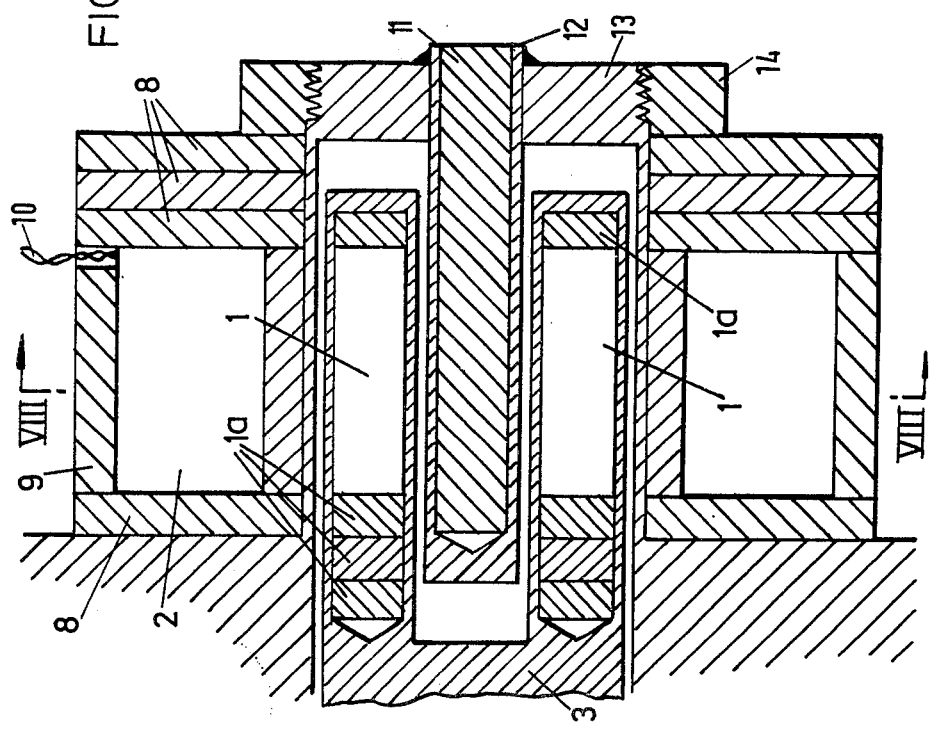

BEARING WEAR DETECTION DEVICES

This invention relates to the detection of wear in bearings in sealed rotor pumps such as are used in the nuclear and chemical fields.

In such pumps, the bearings and rotating shaft are immersed in the fluid being pumped, which is often of a corrosive nature. Changes in the fluid, such as the appearance of particulate matter, may cause the bearings to wear rapidly. It is therefore difficult to predict the life of the bearings for maintenance purposes. It is not normally possible to examine the bearings physically and wear may therefore reach a point at which damage is caused to the equipment, usually by the rotating parts coming into contact with the static parts.

Since chemical pumps are often mounted remotely from easy access, audible or visible warning devices, such as "screamer devices", are not effective. Various arrangements have been proposed, where the first part of the fixed assembly to contact the rotating parts is intended to be damaged or broken, and this damage or breakage causes an indication to be given. For instance, the fixed part may take the form of a thin walled bulb containing gas, or other fluid under pressure, connected to a pressure indicator or pressure detecting switch if a remote signal is required. Alternatively, the lateral movement of the shaft can cause a pair of electrical contacts to make or break, giving an electrical signal.

All these alternatives have two important disadvantages.

Firstly, they are normally damaged or destroyed by their action, and must be replaced when the bearings are replaced. This adds to the expense and it is possible for the replacement to be omitted or incorrectly carried out, thereby rendering the device ineffective when the bearing wear recurs.

Secondly, they give only one warning signal. It is, therefore, not possible, without duplicating the sensor, to give an advance warning when the wear has become excessive and an overriding cutout when the wear has progressed to the point of imminent damage.

According to the present invention there is provided in a sealed rotor pump an electromagnetic system comprising magnet means and a coil mounted on the stator and rotor and arranged such that a voltage is induced in the coil when the rotor rotates eccentrically, with the said voltage depending on the eccentricity.

The magnet means could be a permanent magnet or group of permanent magnets. Alternatively an electromagnetic system could form the magnet means. In the latter case a soft magnetic component may have a separate energizing coil, or it could be magnetized by a steady current applied through the coil in which currents are to be induced.

The voltage provides a continuous indication of the bearing eccentricity in the form of an electrical signal proportional or otherwise related to the eccentricity, and which can be used to provide a visible indication, and permit a number of independent alarm trips to be operated at progressive critical points in the wear of the bearing.

In a preferred form the electromagnet system consists of a coil mounted either inside or outside an extension of the bearing journal and coaxial with it and a permanent magnet mounted inside the journal itself, but not coaxial with it. If the bearing runs true, the rotation of the magnet is coaxial with the coil, so that the total magnetic flux linking with the coil remains unchanged as the journal rotates and no emf is induced in the coil. If, however, the journal is not running true, the axis of rotation of the magnet does not coincide with that of the coil, so that the flux linking the coil changes as the journal rotates, and an alternating emf which is proportional to the eccentricity is induced in the coil.

There are many relative arrangements of the magnet and coil that would achieve the object of the invention, but preferred arrangements intended to increase the induced emf will have soft magnetic pole-piece surrounding the coil and a soft magnetic pole piece opposing the coil, i.e. a pole-piece inside the journal, where the coil is outside or vice versa.

A permanent magnet need not be employed. The necessary field could be provided by a separate energising winding, which may be identical to that in which the emf is induced. In this case, the permanent magnets will be replaced by soft magnetic components.

The method employed to achieve the required result will depend upon the electrical considerations, particularly the electrical safety requirements. Those methods which avoid the use of separate energizing currents will evidently be preferable in this respect, since they minimise the power levels and simplify the measuring circuit. In one arrangement, the induced voltage may be coupled into a measuring circuit by an isolating transformer whose isolation complies with the requirements for intrinsic safety.

In one instance the coil may be in a hazardous area, while the measuring circuit may be coupled to the power circuit of the machine so that it may be automatically cut off, in the event of the bearing wear or journal eccentricity exceeding some preset value.

It must be noted that the characteristics of the measuring circuit must allow for the fact that the journal may wander or precess within a worn bearing, and the signal produced by the device may be highly irregular.

The device described above fulfils the requirements in that all the components may be mounted inside the existing stainless components, and no joints, other than those normally required to assemble the pump are required.

The invention will be further described with reference to the accompanying drawings of various basic arrangements and a preferred embodiment of the invention.

In the drawings:

FIG. 7 is an axial section illustrating a preferred form of the invention;

FIG. 8 is a section on the line VIII—VIII of FIG. 7;

Figure 1:
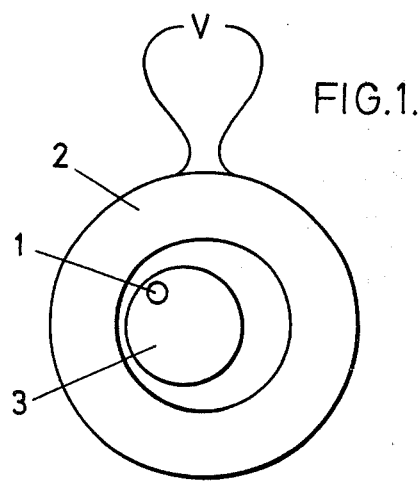
FIGS. 1 to 6 illustrate diagrammatically the various basic arrangements.
Figure 2:
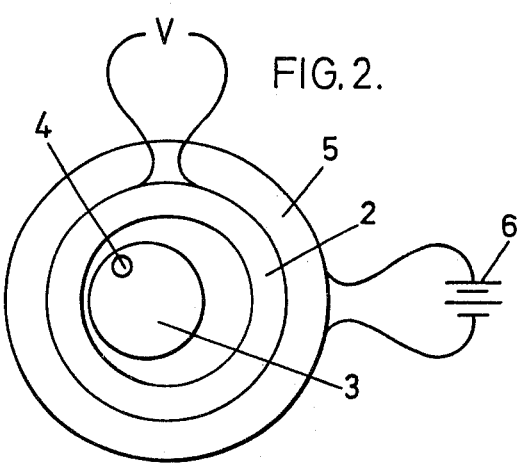

FIG. 1 shows the basic principle of the device, with the permanent magnet 1 moving relative to a stationary coil 2. As the eccentric shaft 3 rotates, a voltage V is induced. The magnet 1 is shown as a rod in section, but other shapes are possible. FIG. 2 shows a similar assembly, having a soft magnetic pole-piece 4 in the shaft 3 and an energising coil 5 with a d.c. power source 6.

Figure 3:
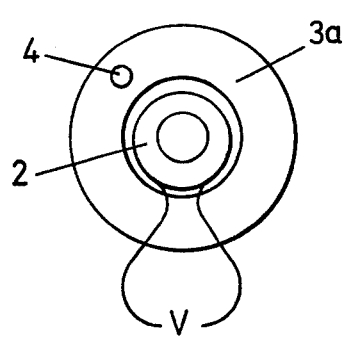
Figure 4:
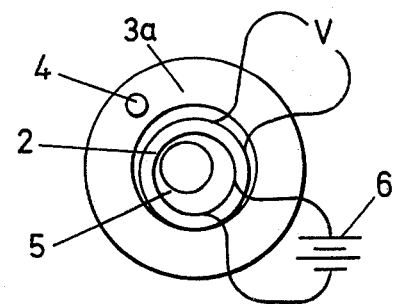

FIGS. 3 and 4 show alternatives to FIGS. 1 and 2 with the coil 2 mounted inside a hollow shaft 3a, but mounted on the stator, with permanent magnet 1 and pole-pieces 4 with exciting coil 5 respectively.

Figure 5:
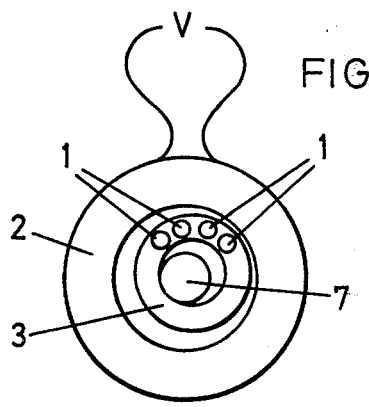

FIG. 5 shows an assembly having an external coil 2, an internal soft magnetic pole-piece 7 within the shaft 3 and a group of four rod magnets 1.

Figure 6:
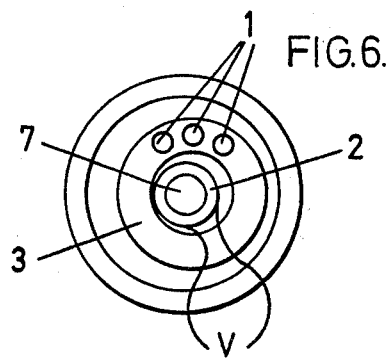

FIG. 6 shows a similar arrangement with an internal coil 2, and with only three magnets 1.

FIGS. 7 and 8 show a preferred arrangement using an external coil 2 so that the coil may be large enough to contain many turns. There are two groups of permanent magnets 1, with one group on each side of the shaft 3, facing opposing directions, and an internal pole-piece 11, as in FIG. 5, all to increase the sensitivity. This is important, since the shaft eccentricity may be of the order of 0.01" and therefore the relative movement of shaft and stator components is very slight and the induced emf correspondingly small.

The construction of this preferred arrangement is intended as a compromise between the greatest sensitivity and simplicity of construction.

The coil 2 is wound on a former (not shown), and surrounded by a soft magnetic circuit consisting of the discs 8 and an outer tube 9. It is mounted on an extension of the stator of the machine. Leads to the coil are shown at 10. In the centre of the stator is a soft magnetic pole-piece 11. The extension of the rotating journal is drilled axially to accommodate the centre pole-piece 11 and the necessary clearance. The pole-piece 11 is mounted in a stainless steel tube 12 welded to an end cap 13 forming part of the stator and having threads for a retaining nut 14 to hold the discs 8 and coil 2 in position. The mounting of the coil 2 and the housing of the centre pole-piece 11 are in stainless steel and are welded into a single component.

The magnets 1 and associated soft magnetic pole-pieces 1a are inserted into holes drilled in the journal extension and the ends of the holes are sealed by welding.

It should be noted that no joints or gaskets are required by this device, and that the assembly of the cavity of the pump is completed by welding, which is used to assemble the rest of the pump.

The action of the device is as follows. As long as the journal rotates coaxially with the stator, the magnetic flux which passes from each magnet is divided in a constant proportion between the central pole-piece 11 and the magnetic circuit 8, 9 surrounding the coil. The proportion is approximately the ratio of the distances between the magnet pole-pieces 1a and the two magnetic stator components 9 and 11.

If the journal is not coaxial, then as it rotates, these two distances change, causing the flux round the coil to change, producing an alternating voltage proportional to the eccentricity and having a frequency equal to the rate of rotation of the journal.

This latter property permits the voltage produced by the rotating magnets to be distinguished from that produced by stray magnetic fields, since the rates of rotation of most forms of motor are not equal to the supply frequency. Frequency-selective circuits can therefore be used to separate these voltages. In practice this problem is minimised by the magnetic circuit surrounding the coil which acts in some measure as an electromagnetic shield.

The voltage produced by the coil can be of the order of 5 volts or more and therefore does not require sensitive amplifiers. If, however, it is to be used to provide a control signal to operate alarms or safety contacts, then it will require some form of amplification to operate the necessary relay.

Figure 9:
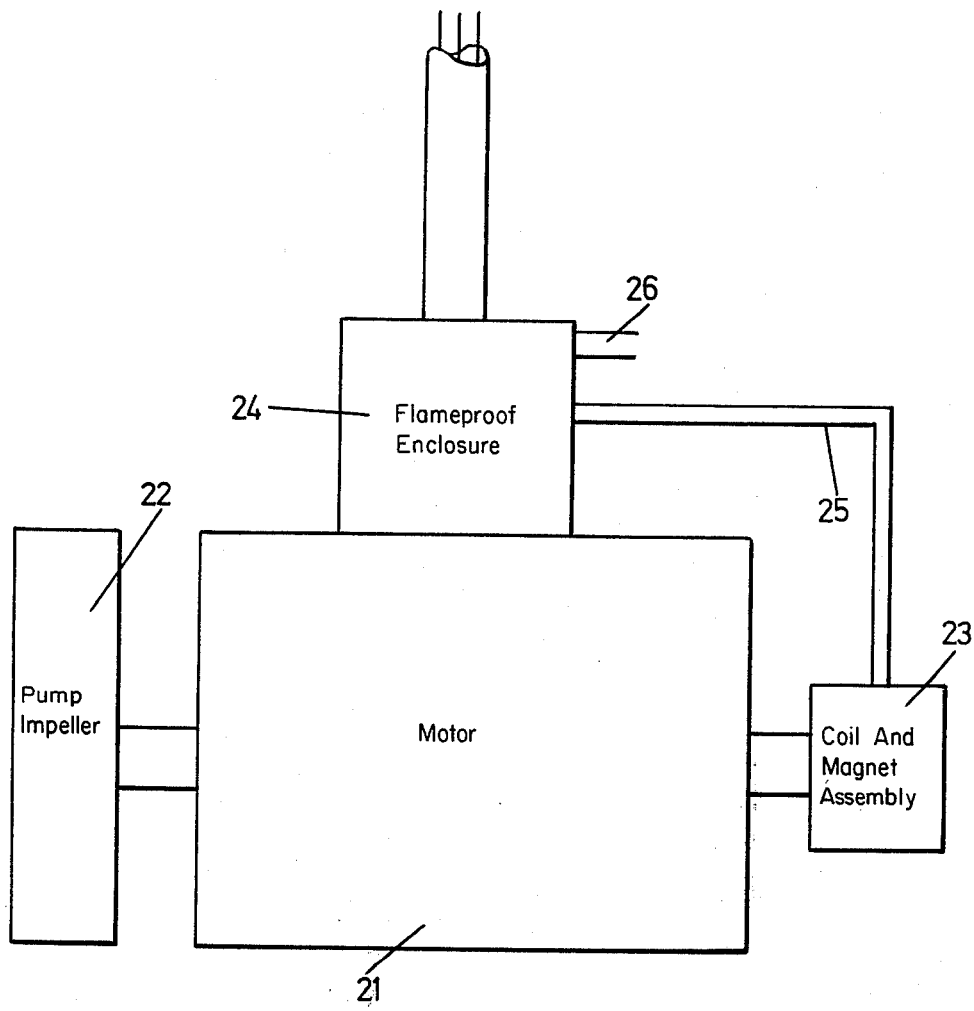
FIG. 9 is a diagrammatic illustration of the relative arrangement of the mechanical and electrical components in a particular application of the invention.

FIG. 9 shows how the assembly would operate in practice with a motor 21 driving a pump impellor 22 and the motor shaft passing into a coil and magnet assembly 23 giving a signal in the event of eccentricity. This signal would be fed to a flameproof enclosure 24 containing the motor contactor and cutout circuitry via lines 25 and monitor signal output is shown at 26.

Figure 10:
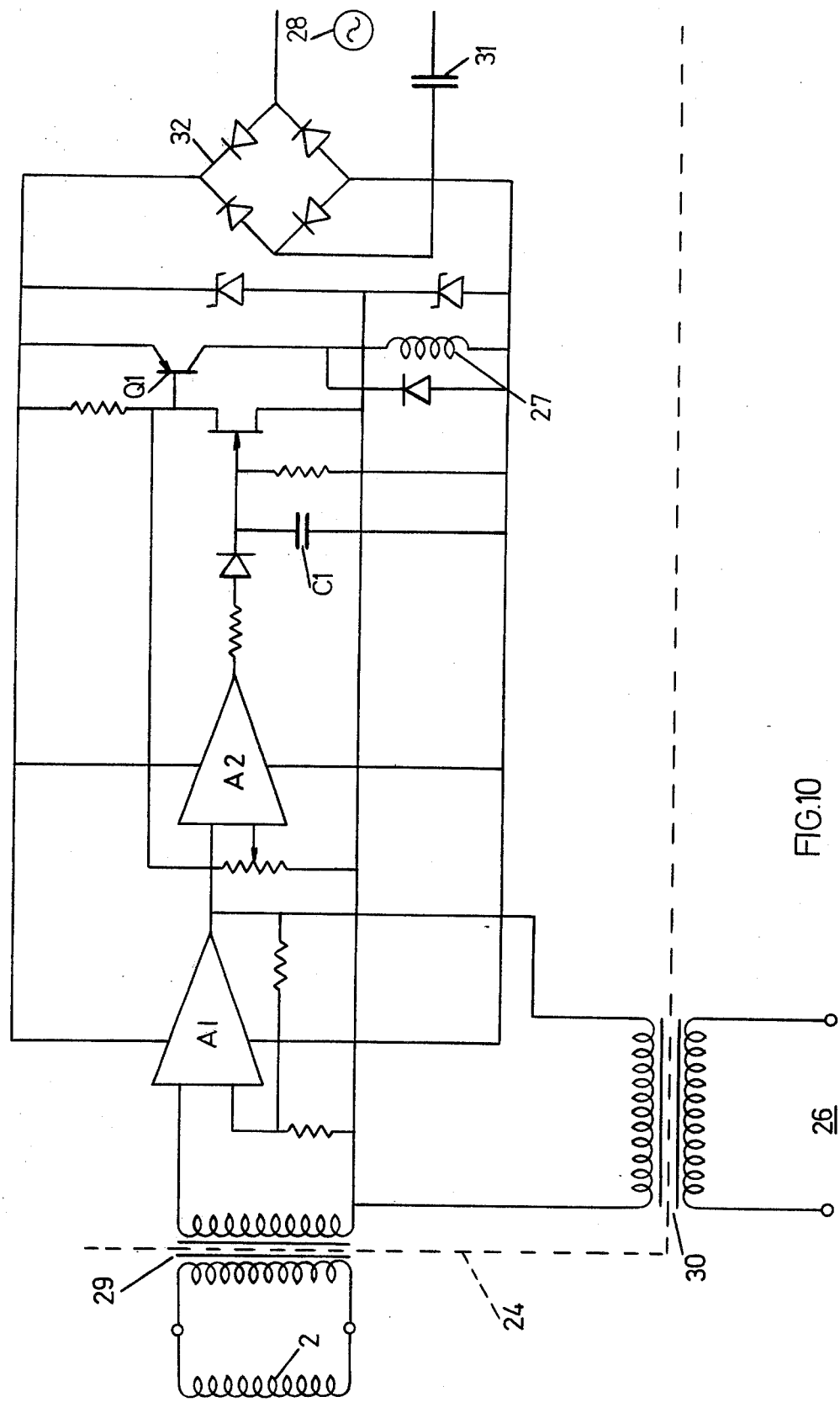
FIG. 10 is a diagram of a form of circuit for use therewith.

FIG. 10 shows one form of circuitry utilizing the signals from the sensing coil 2 to actuate a cutout relay 27 and provide a monitor output for continuous monitoring of the eccentricity.

The coil 2 need not be mounted inside the flameproof enclosure 24, since its impedance is such that it can be made intrinsically safe. Coupling to the detector circuit which may be inside the enclosure 24 and powered from the power supply 28 to the motor, is achieved by a transformer 29, the windings of which are on opposite sides of the flameproof enclosure 24.

An output transformer 30 is also shown for the monitoring output 26 which can be used to monitor the voltage by means of a portable switched, or permanently wired instrument, without the possibility of disturbing the signal to the trip circuit.

Transformer 29 couples the signal across the flameproof enclosure into a high-impedance amplifier A1. Transformer 30 allows the amplified signal to be monitored to indicate the extent of the journal eccentricity. An amplifier A2 compares the peak signal with a fixed setting and charges a capacitor C1 whenever it exceeds a given value. If the set value is exceeded on a sufficient number of successive revolutions, transistor Q1 turns on, and the relay 27 operates. This circuit absorbs very little power and can therefore be operated directly from the high voltage supply 28 to the motor via a dropping resistor or capacitor 31 and a bridge rectifier 32. As soon as transistor Q1 turns on, its drain voltage falls, and the amplifier A2 locks up, since the reference voltage to the potentiometer is obtained from this point. Once the eccentricity has exceeded the set value therefore, the cutout relay 27 will remain energised until the motor is turned off.

Since, in practice there will always be at least a small output from the coil 2 when the magnets rotate relative thereto, means may be provided to sense when the output is zero, and hence the coil is inoperative, to cut-off the power to the motor.

Figure 11:
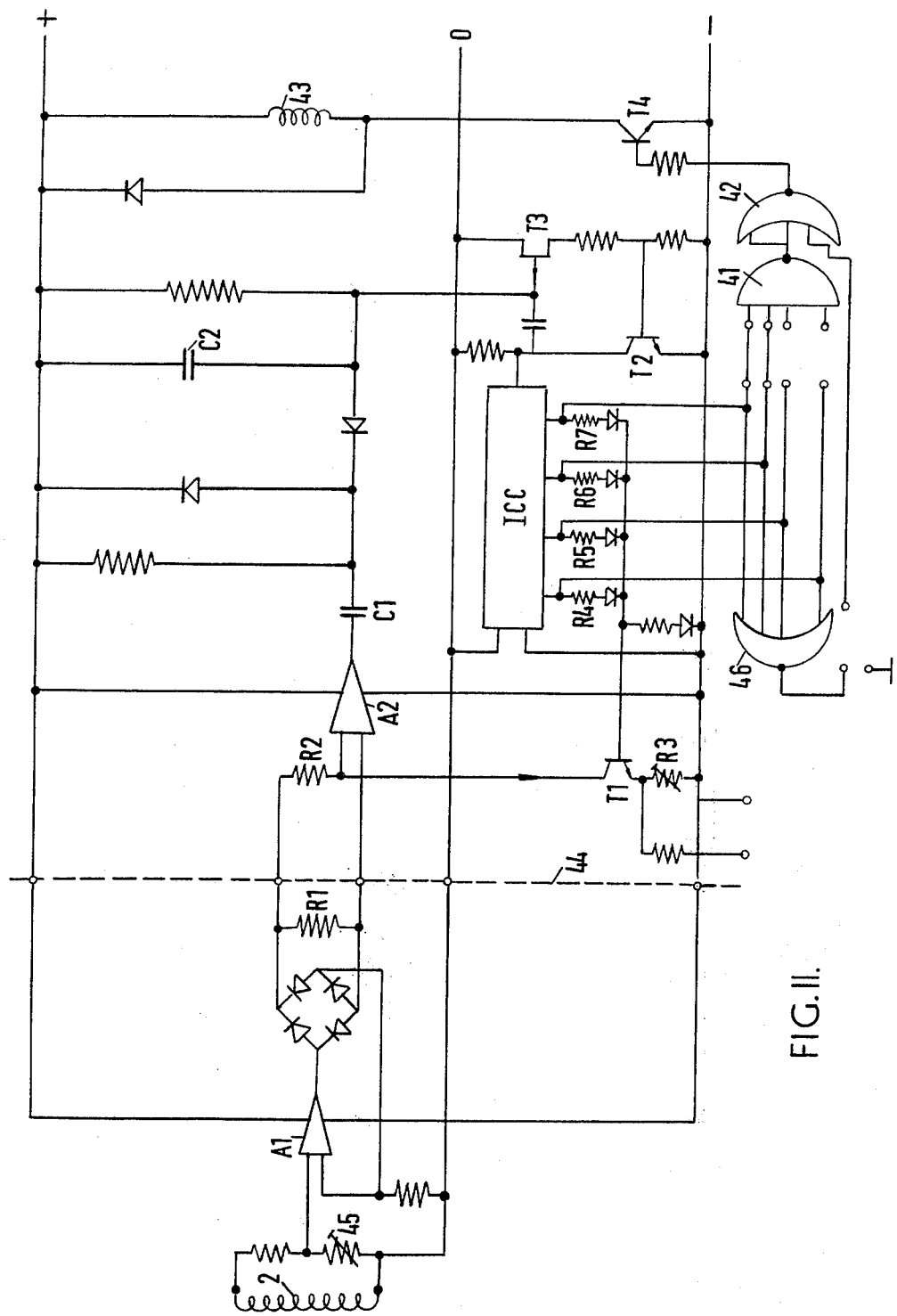
FIG. 11 is a circuit diagram of a further form of circuit for use with the arrangement of FIG. 9.

It is possible for the output from the sensing coil to be used as an indication of the wear on the bearings. However, because the forces on the rotating parts, due to lubrication and loading, may change from time to time, it may happen that, at the time the output of the coil is tested the shaft may be running less eccentrically than is possible should the eccentric forces be different. The true indication of the bearing wear is the maximum output from the coil that has occurred since the bearings were last renewed. For practical considerations, this may be taken as the maximum output since the machine was last energised, since most types of machine to which this device is applicable are likely to run continuously for long periods. FIG. 11 shows a modified form of amplifier for use with the coil which will retain a memory of the greatest output from the coil.

The output from the coil 2 is amplified by an amplifier A1, which gives an amplified signal which is rectified and developed across resistor R1. A reference voltage is generated across resistor R2 by a transistor T1, so that amplifier A2 switches when the eccentricity signal across resistor R1 exceeds the reference voltage. When this occurs on a predetermined number of successive cycles, defined by the ratio between the capacitors C1 and C2 in a diode pump arrangement, field effect transistor T3 switches, generating via transistor T2 a clock pulse for an integrated circuit counter ICC. The counter ICC has four binary outputs connected via appropriately valued resistors R4, R5, R6 and R7 to the base of the transistor T1, so as to provide a combined output signal on the base related to the count. Thus, as the count increases by one, increasing the base current of T1 via the resistor network R4 to R7 which acts as a simple digital to analogue converter, the reference signal across R2 increases. The reference voltage therefore increases, with the arrangement shown, in 16 discrete steps, remaining at one step until the previous greatest signal is exceeded.

An indication of the bearing wear, represented by the count, could be obtained in a number of ways. The simplest of these is to read the voltage across resistor R3, so this is shown as accessible from outside the amplifier, for connection to a simple voltmeter.

If a cutout is required, to operate at a given value of wear, then the setting of this value can be conveniently made by decoding the outputs of the counter ICC. In this way, the setting can be made by links between the counter, and a logic AND gate 41. The gate 41 is shown as having four inputs for selective connection to the outputs of the counter ICC. The floating inputs act as though they have signals on them so the gate 41 can be made to conduct at any value of the counter from 1 to 16. It is shown as conductive at the value 12. The output of the gate 41 is fed to an OR gate 42, an output of which switches a transistor T4 to conduction to energise a cutout relay coil 43 when the set value of the counter is reached.

The amplifier is shown in two parts, divided by a dotted line 44. The part to the left of the line can be mounted with the coil and magnet assembly, and calibrated by means of the potentiometer shown at 45, to give a standard output for a given bearing eccentricity. The other part may be mounted with the motor switchgear from which it is powered, both parts being intrinsically safe if so required.

There will always be a residual signal from the coil 2 due to normal running clearances, so that the count of the integrated circuit counter should never be zero. An OR gate 46 detects the zero condition and causes the cutout to operate. This prevents the machine being operated with the sensing circuit disconnected.

Figure 12:
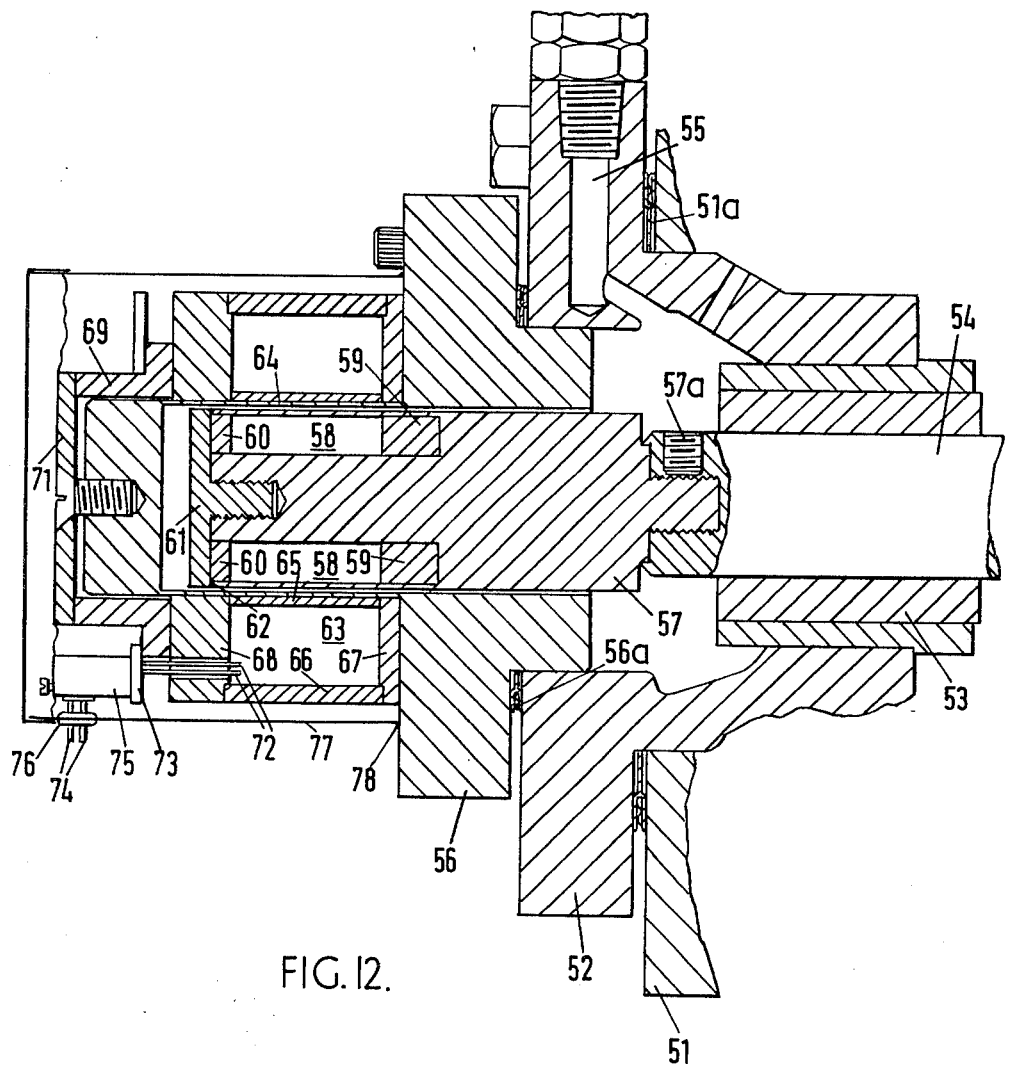
FIG. 12 is a sectional view of an alternative arrangement of the mechanical component.

FIG. 12 shows the rear end 51 of a pump housing to which is secured in conventional manner, with interposition of gasket 51a consisting of a PTFE envelope with a stainless steel insert, a housing 52 for a rear bearing 53 of the pump shaft 54. A recirculating line 55 from the fluid being pumped enters through the housing 52 to provide lubrication. In a conventional sealed or glandless pump, the housing 52 would be solid at its rear end, but in the present arrangement it is closed by an outer housing 56 which coaxially receives an extension bobbin 57 of the shaft 54. A gasket 56a is interposed between the housings 52 and 56. The bobbin 57 is form-lockingly received by a recess at the end of the shaft 54 and secured by a grub screw 57a.

The bobbin 57 has recesses for permanent magnets 58 and inner and outer soft pole-pieces 59 and 60 and an end cap 61 is threadedly received in the end of the bobbin 57 and secured and sealed by welding 62. If desired a soft iron pole may be located axially of the bobbin 57 by the end cap 61.

A stationary coil 63 is arrannged on an extension 64 of the housing 56 coaxially with the bobbin 57 so as to coact with the magnets 58 to produce an emf when the bobbin rotates eccentrically in relation to the coil 63. The coil is arranged in an annular space between inner and outer rings 65, 66 and inner and outer discs 67, 68. These rings and discs are returned by a support collar 69 and an end plate 71 secured to the casing 56. Leads 72 run from the coil to a printed circuit board 73 mounted on the collar 69 and output leads 76 are shown from a potentiometer 75 through a grommet 76 in an aperture in a can 77 which is filled with encapsulating resin after final assembly of the device. The can 77 is secured to the housing 56 by tack welds 78.

Various modifications may be made within the scope of the invention.

I claim:

1. In a glandless sealed rotor pump of the type having a static housing, bearings in said housing, and a rotor mounted in said bearings and wholly contained within said housing: the improvement comprising an electromagnetic bearing wear detection system including magnet means mounted on said rotor and a coil mounted coaxially on said rotor outside said housing immediately adjacent the path of said magnet means as said rotor rotates, said magnet means being mounted eccentrically of said rotor so as to follow a circular path at a constant distance from said coil as said rotor rotates truly in said bearings whereby the flux threading said coil remains constant, but to follow a circular path varying in distance from said coil if said rotor rotates eccentrically whereby the flux threading said coil varies and induces an alternating e.m.f. in said coil, the amplitude of the e.m.f. varying with the eccentricity of said rotor and the frequency of the e.m.f. varying with the speed of rotation of said rotor.

2. A sealed rotor pump as claimed in claim 1, in which said magnet means comprises a permanent magnet arrangement.

3. A sealed rotor pump as claimed in claim 2, in which said magnet arrangement comprises two groups of magnets arranged in opposition.

4. A sealed rotor pump as claimed in claim 1, in which said magnet means comprises an electromagnetic system.

5. A sealed rotor pump as claimed in claim 1, in which said coil is radially outside said magnet means, comprising soft magnetic pole-pieces surrounding said coil and a soft magnetic pole-piece radially inwardly of said magnet means opposing said coil.

6. A sealed rotor pump as claimed in claim 1, comprising a measuring circuit and a cut out, in which the voltage signal is fed into a memory and which energizes said cut out when the signal level exceeds a given level.

7. A sealed rotor pump as claimed in claim 6, in which the measuring circuit is also arranged to give a continuous indication of the signal level.

8. A sealed rotor pump as claimed in claim 6, including a full wave rectifier in the measuring circuit.

9. A sealed rotor pump as claimed in claim 6, in which the signal from the coil is developed across a variable potentiometer for calibration purposes and applied to a first amplifying stage.

10. A glandless sealed rotor pump having a static housing, bearings in said housing and a rotor mounted in said bearings and wholly contained within said housing and including an electromagnetic system comprising magnet means and a coil, one of said magnet means and coil being mounted on said rotor and the other of said magnet means and coil being mounted on said stator, said magnet means and coil being arranged such that a voltage is induced in said coil when said rotor rotates eccentrically with respect to said stator, with the voltage depending on the eccentricity, a measuring circuit, means for electrically coupling said coil to said measuring circuit, a cut out operatively connected to said measuring circuit, said measuring circuit energizing said cut out when the signal level exceeds a given level, and said measuring circuit including a memory device to record the maximum signal level since the circuit was energized.

11. A sealed rotor pump as claimed in claim 10, in which the memory device is a counter having an output controlling a reference signal, and the circuit includes means to detect when the voltage signal from the coil exceeds a level related to the reference signal, and to pulse the counter to increase the reference signal when the voltage signal exceeds the said level.

12. A sealed rotor pump as claimed in claim 11, in which means is provided for energizing the cut out when the counter reaches a predetermined setting.

13. A sealed rotor pump as claimed in claim 11, further comprising means for energizing the cut-out when the counter is at zero.

14. A sealed rotor pump as claimed in claim 11, comprising a circuit including a diode and a capacitor which is clamped through the diode to detect when the signal from the coil exceeds the reference signal for a predetermined time.

* * * * *